US009637347B2

(12) United States Patent
Savchenko

(10) Patent No.: US 9,637,347 B2
(45) Date of Patent: May 2, 2017

(54) HOSE STORAGE SYSTEM

(71) Applicant: Paul Aaron Savchenko, Sequim, WA (US)

(72) Inventor: Paul Aaron Savchenko, Sequim, WA (US)

( * ) Notice: Subject to any disclaimer, the term of this patent is extended or adjusted under 35 U.S.C. 154(b) by 138 days.

(21) Appl. No.: 14/617,795

(22) Filed: Feb. 9, 2015

(65) Prior Publication Data

US 2016/0229664 A1   Aug. 11, 2016

(51) Int. Cl.
*B65H 75/44* (2006.01)
*B65H 75/36* (2006.01)

(52) U.S. Cl.
CPC ....... *B65H 75/368* (2013.01); *B65H 2701/33* (2013.01)

(58) Field of Classification Search
CPC ....... B65H 75/44; B65H 75/36; B65H 75/368
See application file for complete search history.

(56) References Cited

U.S. PATENT DOCUMENTS

| 3,160,360 | A | * | 12/1964 | Lukas | B63B 35/816 242/388.91 |
|---|---|---|---|---|---|
| 3,653,401 | A | | 4/1972 | Beeler et al. | |
| 3,831,870 | A | | 8/1974 | Daniel | |
| 5,117,859 | A | * | 6/1992 | Carlson | B65H 75/368 137/355.25 |
| 5,392,808 | A | | 2/1995 | Pierce | |
| 7,104,491 | B2 | | 9/2006 | Vinding | |
| 7,121,276 | B2 | | 10/2006 | Jagger et al. | |
| 7,931,021 | B2 | | 4/2011 | Livingston et al. | |
| 8,191,551 | B2 | | 6/2012 | Skovgard | |
| 8,282,050 | B2 | | 10/2012 | Georgey | |
| 2006/0186254 | A1 | | 8/2006 | Handley et al. | |
| 2006/0243282 | A1 | | 11/2006 | Sackman et al. | |
| 2010/0307496 | A1 | | 12/2010 | Lueckenhoff | |
| 2011/0266383 | A1 | | 11/2011 | Cohen et al. | |
| 2013/0187011 | A1 | | 7/2013 | Rifenburg | |

(Continued)

FOREIGN PATENT DOCUMENTS

| WO | WO2011009125 A1 | 1/2011 |
|---|---|---|
| WO | WO2013057621 A1 | 4/2013 |
| WO | WO2013115639 A1 | 8/2013 |

OTHER PUBLICATIONS

Ordering & Accessory Guide, Hannay Reels, 2013, 20 pages.
Peter Chun et al., "Oxygen Concentrator Tube Storage Sanitation Device", University of Michigan, Dec. 11, 2012, 237 pages.

*Primary Examiner* — Sang Kim
(74) *Attorney, Agent, or Firm* — Lempia Summerfield Katz LLC

(57) ABSTRACT

In order to keep hose for oxygen delivery off of the floor and thus make use of the oxygen delivery system safer, a storage system for storing the hose includes a support structure, a first pulley assembly, and a second pulley assembly below the first pulley assembly. At least a part of the first pulley assembly is translationally fixed relative to the support structure, and the second pulley assembly is translationally movable relative to the first pulley assembly, along the support structure. The hose is wrapped around pulleys of the first pulley assembly and pulleys of the second pulley assembly, and the amount of hose stored in the storage system is dependent on a position of the second pulley assembly relative to the first pulley assembly.

16 Claims, 4 Drawing Sheets

(56) References Cited

U.S. PATENT DOCUMENTS

| | | | | |
|---|---|---|---|---|
| 2014/0224914 A1* | 8/2014 | Sugiura | ............... | B65H 75/48 242/379 |
| 2014/0246534 A1* | 9/2014 | Sugiura | ............... | B65H 75/48 242/388.9 |
| 2014/0274516 A1* | 9/2014 | Sugiura | ............... | B65H 75/48 474/150 |

* cited by examiner

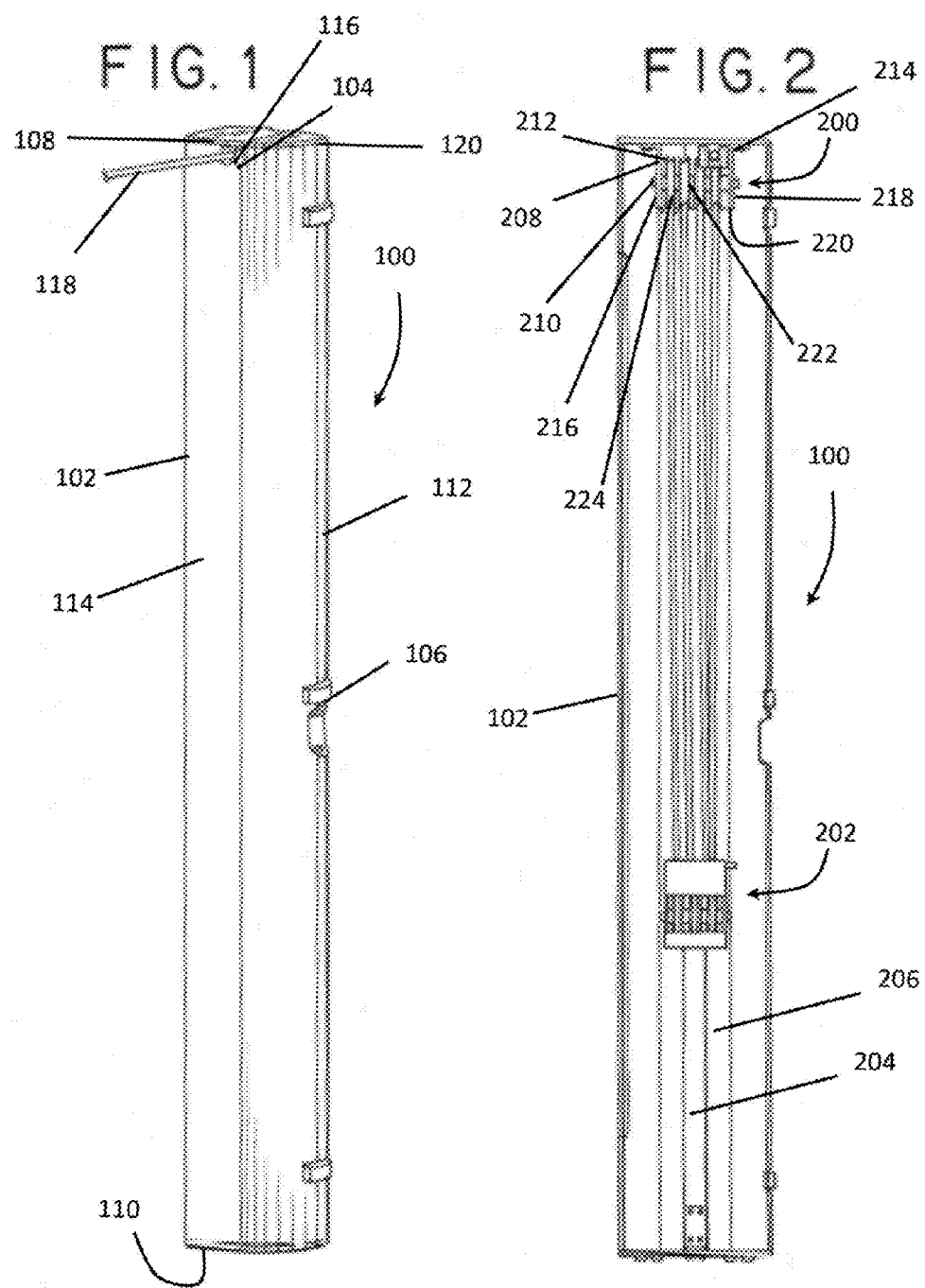

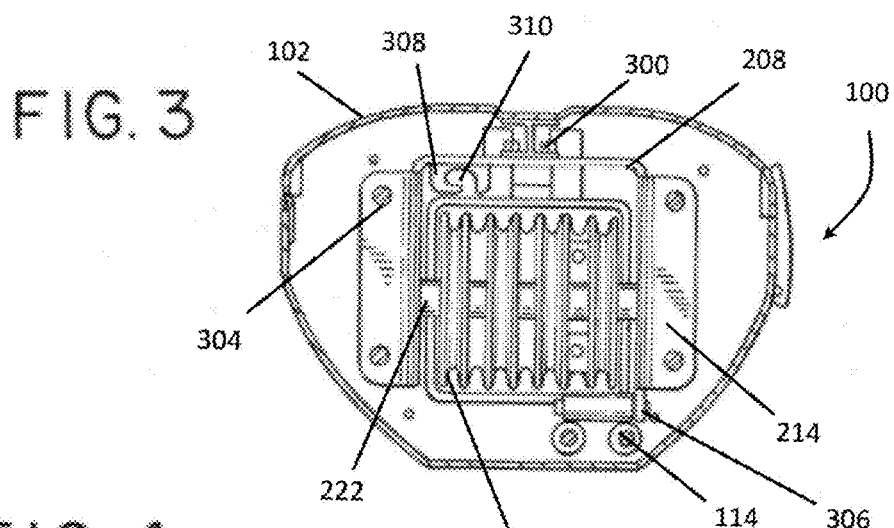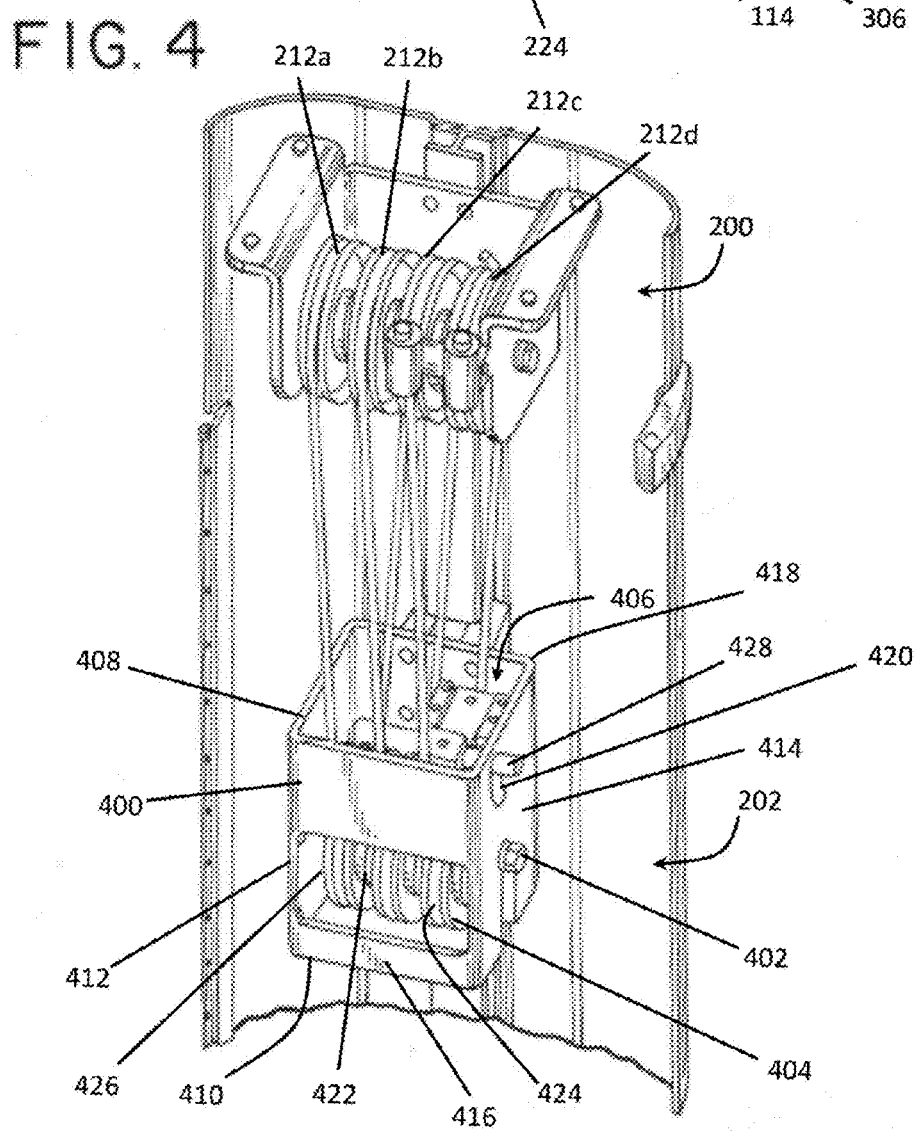

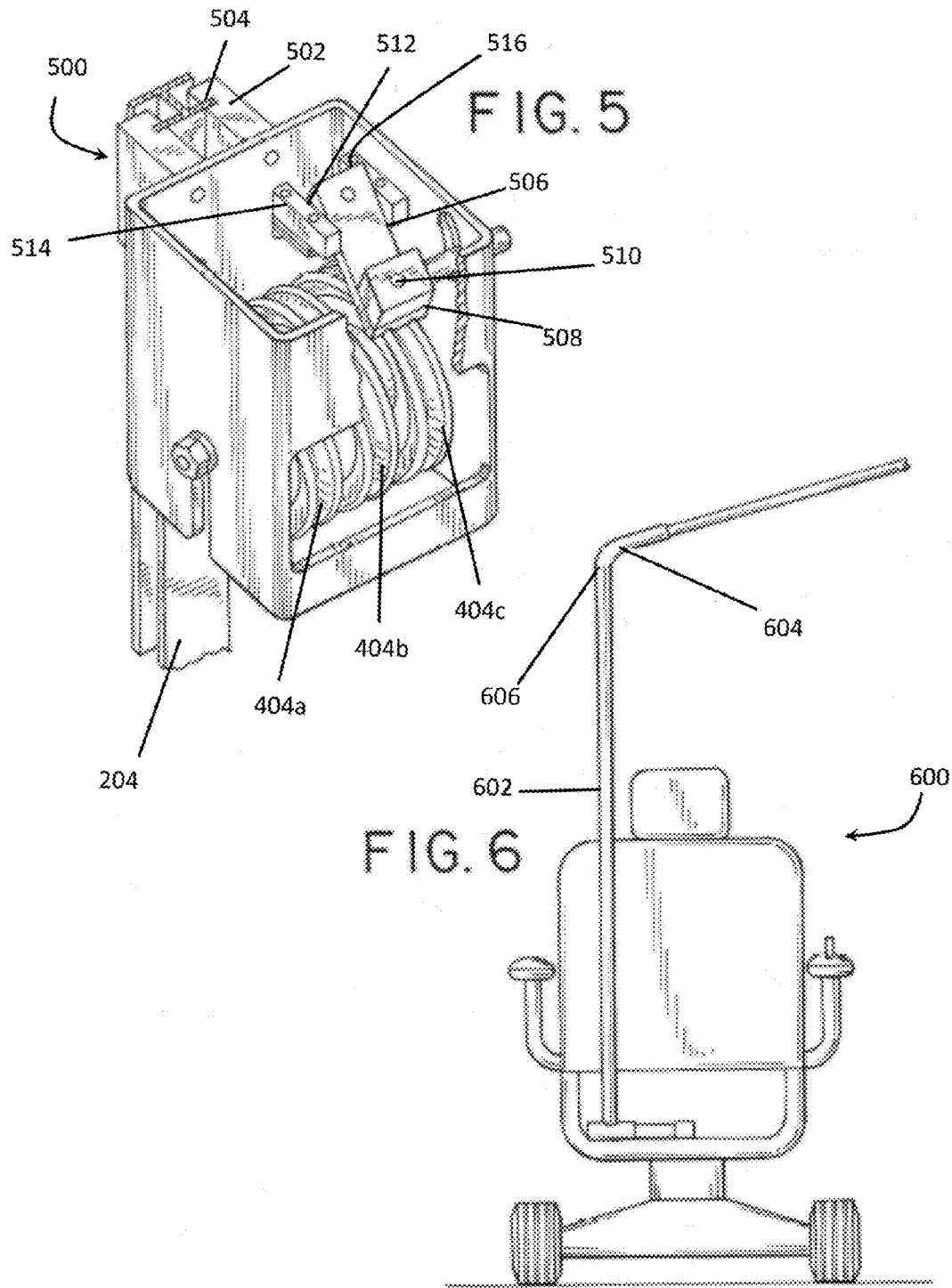

HOSE STORAGE SYSTEM

FIELD

The present embodiments relate to a hose storage system.

BACKGROUND

In-home oxygen delivery for a patient may use a long length (e.g., 25 feet or 50 feet) of rubber tubing to provide oxygen from an oxygen concentrator to the patient who moves around the home using a scooter, a wheel chair, or by walking. The length of hose typically lies on the floor and is a tripping hazard for the patient moving around the home and/or an attendant such as a nurse attending to the patient. Additionally, the oxygen flow through the hose may become obstructed by kinking of the hose caused by the patient, the attendant, furniture in the home, or other people or objects that come in contact with the hose.

SUMMARY

In order to keep hose for oxygen delivery off of the floor and thus avoid kinking and obstruction and make use of the oxygen delivery system safer, a storage system for storing the hose includes a support structure, a first pulley assembly, and a second pulley assembly below the first pulley assembly. At least a part of the first pulley assembly is translationally fixed relative to the support structure, and the second pulley assembly is translationally movable relative to the first pulley assembly, along the support structure. The hose is wrapped around pulleys of the first pulley assembly and pulleys of the second pulley assembly, and the amount of hose stored in the storage system is dependent on a position of the second pulley assembly relative to the first pulley assembly.

In a first aspect, a storage system for storing a length of a tubular structure is provided. The storage system includes a support structure. The storage system also includes a first pulley assembly that includes a plurality of first pulleys. At least a part of the first pulley assembly is translationally fixed relative to the support structure. The plurality of first pulleys are rotatable about a first axis of rotation. The storage system also includes a second pulley assembly translationally movable relative to the first pulley assembly, along the support structure. The second pulley assembly includes at least one second pulley. The at least one second pulley is rotatable about a second axis of rotation.

In a second aspect, a hose storage system includes a housing including an opening at or adjacent to a top edge of the housing. The hose storage system also includes a rail extending along at least a portion of the housing. The hose storage system includes at least two first pulleys rotatable about a first axis. The at least two first pulleys are fixed translationally relative to the rail. The hose storage system also includes at least one second pulley rotatable about a second axis. The at least one second pulley is movable translationally relative to the rail beneath the at least two first pulleys, in a direction along the rail. The hose storage system includes a hose connector fixed positionally relative to the rail. The hose connector includes an input and an output. The input is connectable to a gas or fluid source. The output is connectable to a hose extending at least from the hose connector, to a first pulley of the at least two first pulleys, partially around the first pulley of the at least two first pulleys, and to a first pulley of the at least one second pulley. The hose further extends partially around the first pulley of the at least one second pulley, to a second pulley of the at least two first pulleys, and partially around the second pulley of the at least two first pulleys. The hose exits the housing through the opening.

In a third aspect, a method for extending a portion of a hose stored in a hose storage system to a user is provided. The hose storage system includes a structure, and a lower pulley assembly and an upper pulley assembly supported by the structure. The lower pulley assembly includes one or more pulleys. The upper pulley assembly includes two or more pulleys. The hose is wrapped partially around the two or more pulleys of the upper pulley assembly and partially around the one or more pulleys of the lower pulley assembly. The hose exits the hose storage system through an opening in the hose storage system. The method includes moving the lower pulley assembly towards the upper pulley assembly in response to a force applied to the hose. At least a part of the upper pulley assembly is positionally fixed relative to the structure. The movement of the lower pulley assembly towards the upper pulley assembly releases the portion of the hose through the opening in the hose storage system.

BRIEF DESCRIPTION OF THE DRAWINGS

FIG. 1 shows a perspective view of one embodiment of a hose storage system with a door closed;

FIG. 2 shows a front view of the hose storage system of FIG. 1 with the door removed;

FIG. 3 shows a top view of the hose storage system of FIG. 2 with the top removed;

FIG. 4 shows a perspective view of one embodiment of a first pulley assembly and a second pulley assembly for the hose storage system of FIG. 2;

FIG. 5 shows a perspective view of the second pulley assembly of FIG. 4;

FIG. 6 shows one embodiment of a movable patient device; and

DETAILED DESCRIPTION

Figure 7:
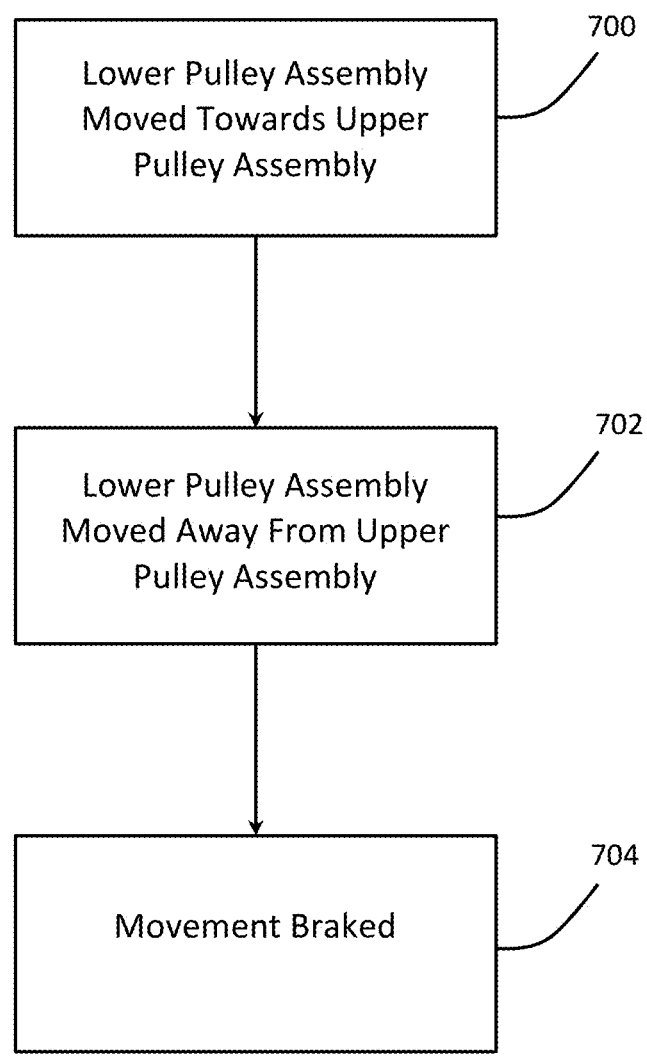
FIG. 7 shows one embodiment of a method for providing a portion of a hose to a user.

A retractable hose reel system that keeps oxygen tubing off of the floor for a patient requiring oxygen in the home of the patient is disclosed herein. The disclosed retractable hose reel system includes a freestanding cabinet having a number of pulleys mounted side by side on a fixed bracket mounted at the top of the cabinet. A number of pulleys are also mounted on a lower bracket that slides up and down on a track the full height of the cabinet. An outer guide pulley guides a hose from a position of the user into the cabinet, where the hose is stored on the pulleys of the fixed bracket and the pulleys of the slidable lower bracket. The lower bracket includes a brake mechanism. The brake mechanism may be turned on or off to prevent or allow, respectively, the lower bracket to slide relative to the track. In use, the hose is routed from an oxygen concentrator into the cabinet, where the hose alternately loops over the fixed and movable pulleys so that more or less hose may be accommodated within the cabinet depending on a position of the lower bracket. This keeps a portion of the hose safely within the cabinet and not on the floor where the hose may be tripped over or crushed.

FIG. 1 shows one embodiment of a hose storage system 100. The hose storage system includes a housing 102, one or more rollers 104, and locks 106. The housing 102 includes a top 108, a bottom 110, and at least one side 112. The housing 102 includes one or more doors 114 (e.g., a door that is hinged to a stationary portion of the housing 102) that form at least a portion of the at least one side 112. The door 114 may be closed to hide components of the hose storage system 100 from view of a user outside of the housing 102. Alternatively, the housing 102 may include a non-closeable opening to provide the user with access to the components of the hose storage system 100, for example.

The housing 102 may be made of any number of materials including, for example, wood, plastic (e.g., ultra-high-molecular-weight (UHMW) polyethylene), metal, another material, or any combination thereof. The housing 102 may be any number of dimensions. The dimensions of the housing 102 may be set by the amount of hose to be stored and/or the number of pulleys within the hose storage system 100. The larger the number of pulleys used within the hose storage system 100, the shorter the housing 102 may be.

The housing 102 may be fixed to a surface of a room (e.g., a wall and/or the floor that supports the hose storage system 100). In one embodiment, the housing 102 is not fixed to a surface of the room, but the weight of components within the housing 102 keeps the housing 102 stationary relative to the floor. In another embodiment, the hose storage system 100 includes wheels, such that the hose storage system 100 is movable relative to the floor. The hose storage system 100 may be movable relative to the floor in other ways (e.g., using sliders and tracks).

The one or more rollers 104 may be positioned on a side of the housing, at, adjacent, or near the top 108 of the housing. In the embodiment shown in FIG. 1, the one or more rollers 104 include three rollers. The three rollers 104 are positioned around an opening 116 (e.g., below, to the left, and to the right of the opening), into and out of which hose 118 stored in the hose storage system 100 moves. One of the rollers 104 may rotate about an axis that is parallel with a surface that supports the housing 102, and the other rollers 104 may rotate about parallel axes that are perpendicular to the surface that supports the housing 102, respectively. The rollers 104 facilitate movement of the hose 118 into and out of the hose storage system 100.

The opening 116 in the housing 102, through which the hose 118 extends, may be any number of sizes and shapes. For example, the opening 116 may be sized to accommodate a large number of hose sizes (e.g., outside diameters). The opening 116 may be positioned near, at, or adjacent to a front-top edge 120 of the housing 102 of the hose storage system 100. In other embodiments, the housing 102 may include more openings or no openings, and/or the opening 116 may be positioned differently on the housing 102 (e.g., through the top 108).

The rollers 104 are attached to the housing 102 such that the rollers 104 are operable to rotate with motion of the hose 118, for example. The rollers 118 may be at least partially made of plastic (e.g., UHMW plastic) to reduce wear on the hose 118. Other materials may be used. More or fewer rollers 104, different configurations of the rollers 104, and/or different positions of the opening 116 and the rollers 104 may be provided.

The locks 106 may be provided on the housing 102 to keep the one or more doors 114 shut during use of the hose storage system 100, for example. The embodiment shown in FIG. 1 shows three locks 106. More or fewer locks may be provided. The locks 106 may be extensions that move into corresponding grooves or slots in the door 114 (e.g., friction fit). The locks 106 may be attached to the housing 102 in any number of ways including, for example, with screws and/or nut/bolt combinations. The locks 106 may be rotatable or may be fixed. Any number of other fasteners may be used to keep the one or more doors 114 shut. In one embodiment, the hose storage system 100 does not include locks.

FIG. 2 shows a front view of the hose storage system 100 of FIG. 1 with the door 114 removed. The components positioned within the housing 102 include a first pulley assembly 200, a second pulley assembly 202, and a rail 204.

The rail 204 is attached to an internal surface 206 of the housing 102. For example, the rail 204 may be attached to a rear, vertical, internal surface 206, as shown in FIG. 2. In one embodiment, the rail 204 extends the entire height of the internal surface 206. In another embodiment, the rail 204 extends less than the entire height of the internal surface 206. The rail 204 is attached to the internal surface 206 in any number of ways including, for example, with screws, nut-bolt combinations, and/or an adhesive. Other fasteners may be used. In one embodiment, the rail 204 may be an integral part of the housing 102. In other words, the rail 204 may be formed of the same material as the housing 102 and as a contiguous or integral part of the housing.

In one embodiment, the rail 204 is an H-beam or an I-beam. In another embodiment, the rail 204 is formed by two lengths (e.g., extrusions) of C-channel attached to each other (e.g., with nut/bolt combinations). Flanges (e.g., four flanges) of the rail 204 may extend in a direction parallel to at least a portion of the internal surface 206. In other embodiments, the rail 204 may be other shapes. For example, the rail may have a uniform square or rectangular cross-section. The rail 204 may be made of any number of materials including, for example, aluminum and/or plastic (e.g., UHMW polyethylene). Other materials may be used for the rail 204.

The first pulley assembly 200 is positioned above the second pulley assembly 202 near, at, or adjacent to the top 108 of the housing 102 for efficient use of space within the housing 102. The top 108 of the housing 102 may be a side of the housing 102 furthest away from a surface that supports the hose storage system 100. As shown in the embodiments of FIGS. 2 and 3, the rail 204 extends the entire height of the housing 102, and the first pulley assembly 200 is attached to the rail 204. In another embodiment, the rail 204 does not extend the entire height of the housing 102, and the first pulley assembly 200 is attached to the housing 102 between a top end of the rail 204 (e.g., the end of the rail 204 furthest away from the surface that supports the hose storage system 100) and the top 108 of the housing 102. Additionally or alternatively, the first pulley assembly 200 may be attached to another internal surface (e.g., the internal top surface) of the housing 102. In one embodiment, the first pulley assembly 200 is not attached to any surfaces of the housing 102. For example, the first pulley assembly 200 may be suspended from a surface, and/or the housing 102 is open on top, and the first pulley assembly 200 is connected to the ceiling of a room, in which the hose storage system 100 is positioned, or is connected to another surface.

The first pulley assembly 200 is fixed translationally relative to the housing 102. The first pulley assembly 200 may be "fixed translationally" in that a housing of the first pulley assembly 200 is attached to the housing 102 and/or the rail 204 and does not move (e.g., translationally, or translationally and rotationally) relative to the housing 102, while allowing for translational and rotational movement of pulleys along and about a shaft of the first pulley assembly 200.

The first pulley assembly 200 includes a housing 208, a shaft 210, and a plurality of pulleys 212 (e.g., pulleys 212a, 212b, 212c, and 212d). In the embodiment shown in FIG. 2, the housing 208 of the first pulley assembly 200 includes one or more flanges 214 (e.g., two flanges) and is attached to the housing 102 (e.g., the top 108 of the housing 102) of the hose storage system 100 using, for example, screws (e.g., four screws) through the one or more flanges 214 and the housing 102 of the hose storage system 100. The housing 208 of the first pulley assembly 200 may be attached to the housing 102 of the hose storage system 100 in any number of other ways including, for example, with nut/bolt combinations, an adhesive, another fastener, or any combination thereof.

The housing 208 includes a first side 216, a second side 218, and a back 220. The housing 208 of the first pulley assembly 200 of the embodiment shown in FIGS. 2-4 is rectangular in shape. For example, the housing 208 is a piece of sheet metal formed into a rectangular shape. In one embodiment, the piece of sheet metal is formed such that the housing 208 does not include a top, a front, or a bottom. In another embodiment, the housing 208 is a rectangular tube or a square tube. In yet another embodiment, none of the sides are completely open, and one or more sides are removable (e.g., the bottom). Sides of the housing 208 (e.g., the bottom) may include one or more openings machined out of or formed or provided through the housing 208, for example, to provide access to the plurality of pulleys 212. The housing 208 may be any number of other shapes and/or may be formed by individual sides or plates attached together via one or more types of fasteners (e.g., nut/bolt combinations and/or screws).

The housing 208 may be made of any number of materials. For example, the housing 208 may be made of aluminum sheet metal or rectangular tube. Alternatively or additionally, the housing 208 may be made of one or more other materials. For example, one or more sides of the housing 208 may be made of plastic (e.g., UHMW polyethylene). Other materials may be used.

The shaft 210 extends across the entire length of the housing 208 in this example, through openings in the first side 216 and the second side 218. In one embodiment, openings in the first side 216 and the second side 218 may include bearings in which the shaft 210 rotates. The shaft 210 is cylindrical in shape and may be made of any number of materials including, for example, UHMW polyethylene. The shaft 210 may be any number of dimensions. For example, the shaft 210 may be 7.0 mm in diameter and may extend across the entire housing 208. Other configurations may be provided.

The shaft 210 may be attached to the housing 208 such that the shaft 210 does not translate or minimally translates along an axial direction in which the shaft 210 extends from the first side 216 to the second side 218 and/or such that the shaft 210 does not rotate, for example. In one embodiment, the shaft 210 is threaded on one end (e.g., the shaft 210 is a bolt threaded on one side), and a nut is used to attach the shaft 210 to the housing 208.

In the embodiment shown in FIG. 2, the plurality of pulleys 212 includes four pulleys 212 (e.g., pulleys 212a, 212b, 212c, and 212d) positioned along the shaft 210. In other embodiments, the plurality of pulleys 212 includes more or fewer pulleys. In another embodiment, only one pulley 212 is positioned on the shaft 210.

The plurality of pulleys 212 may be spaced along the shaft 210 using, for example, spacers 222 (e.g., three spacers 222 between pairs of pulleys of the plurality of pulleys 212, respectively). Other spacers may be provided outside the outermost pulleys of the plurality of pulleys 212 (e.g., pulleys 212a and 212d). The spacers 222 may be made of any number of materials and may have any number of dimensions. For example, at least some of the spacers 222 may have an inner diameter of 7.0 mm and an outer diameter of 1.0 inch. The spacers 222 may have variable width. For example, the spacer 222 closest to the second side 218 may have a greater width than the other spacers 222. The spacers 222 may provide pressure on the plurality of pulleys 212 such that the plurality of pulleys 212 do not translate along the shaft 210. The spacers 222 may be dimensioned such that the plurality of pulleys 212 are free to rotate. The spacers and pulleys may instead or also be mechanically locked (e.g., by keys and ways or detents and recesses) so as to rotate together. In one embodiment, each pulley of the plurality of pulleys 212 may rotate relative to the other pulleys of the plurality of pulleys 212. For example, each pulley of the plurality of pulleys 212 may include bearings such that the pulley may rotate relative to the other pulleys of the plurality of pulleys 212.

Each pulley of the plurality of pulleys 212 may be made of any number of materials including, for example, aluminum or plastic (e.g., UHMW polyethylene). Other materials may be used for the plurality of pulleys 212. Each pulley of the plurality of pulleys 212 may have any number of dimensions. For example, for each pulley of the plurality of pulleys 212, a groove 224 between two annular flanges (see FIG. 3) of the pulley 212 may be sized to fit a particularly dimensioned hose to be stored in the hose storage system 100. The flanges may be dimensioned such that the particularly dimensioned hose remains on the plurality of pulleys 212 during operation of the hose storage system 100. In one embodiment, the groove 224 and the flanges may be sized to fit a large number of different sizes of hoses to be stored in the hose storage system 100.

The first pulley assembly 200 may include additional components. For example, the first pulley assembly may include a hose connector that is connected to the housing 208 at or near, for example, the back 220 of the housing 208. The hose connector is connected to the housing 208 in any number of ways including, for example, a welding, one or more fasteners, an adhesive, another connector, or any combination thereof. The hose connector may be connected to the housing 208 at or near a side (e.g., the first side 216) of the housing 208. In one embodiment, the hose connector is connected to the housing 102 of the hose storage system 100 or is connected to another part of the hose storage system 100. The connector 206 is made of any number of materials including, for example, metal (e.g., aluminum or stainless steel) and/or plastic.

The hose connector may, for example, be a barbed coupler. The barbed coupler includes a first end and a second end. The first end may be outside the housing 208, while the second end may be inside the housing 208. In other words, the barber coupled may be positioned at least partially outside of the housing 208 of the first pulley assembly 200. Alternatively, the hose connector may be positioned entirely within the housing 208 of the first pulley assembly 200, and the first end of the barbed coupler is closer to a bottom edge of the housing 208 than the second end of the barbed coupler. The barbed coupler may extend between the first end and the second end in a direction parallel with the rail 204, for example. In one embodiment, the barbed coupler is aligned with the groove 224 of the pulley 212a. Other orientations may be provided, and other connectors may be used.

The barbed coupler includes a first barb at and adjacent to the first end (e.g., extending inwards from the first end) and a second barb at and adjacent to the second end of the barbed coupler (e.g., extending inwards from the second end). An outer diameter of at least a portion of the first barb is matched to fit an inner diameter of a fixed length of hose. In other words, the outer diameter of at least the portion of the first barb is the same as or greater than the inner diameter of the fixed length of hose. An outer diameter of at least a portion of the second barb is matched to fit an inner diameter of the hose 118. In other words, the outer diameter of at least the portion of the second barb is the same as or greater than the inner diameter of the hose 118. The fixed length of hose and the hose 118 may, for example, be rubber hoses.

The hose connector acts as a hose interface for the first pulley assembly 200. For example, the fixed length of hose runs from a fluid source (e.g., an oxygen concentrator) located within or outside of the hose storage system 100, to the first barb. A first end of the hose 118, which is wrapped around the plurality of pulleys 212 and pulleys of the second pulley assembly 202, and is to be stored within and/or released from the hose storage system 100, is attached to the second barb of the barbed coupler. The fluid from the concentrator, for example, may thus pass through to the hose 118 via the fixed length of hose and the barbed coupler.

FIG. 3 shows a top view of the hose storage system 100 of FIG. 2 with the top removed. FIG. 3 shows one embodiment of the connection of the housing 208 of the first pulley assembly 200 to the rail 204 of the hose storage system 100 with fasteners 300 (e.g., four nut/bolt combinations). The housing 208 of the first pulley assembly 200 may be attached to the rail 204 in any number of ways. For example, the housing 208 may be welded to the rail 204.

FIG. 3 shows the flanges 214 used to attach the first pulley assembly 200 to the housing 102 of the hose storage system 100. In the embodiment shown in FIG. 3, the housing 208 includes two flanges 214. The housing 208 may include more or fewer flanges 214. The flanges may include openings 304 (e.g., four openings) for attaching the housing 208 of the first pulley assembly 200 to the housing 102 of the hose storage system 100. Screws, bolts, and/or other fasteners may extend through the openings 304 and may be used to attach the housing 208 of the first pulley assembly 200 to the housing 102 of the hose storage system 100.

FIG. 3 shows additional components of the first pulley assembly 200. For example, the housing 208 includes a holder 308. The holder 308 may replace the hose connector described above. The holder 308 includes a slot 310, through which the hose 118 extends. The holder 308 keeps the hose 118 properly positioned within the first pulley assembly 200. The hose 118 extends through the holder 308 to the concentrator inside or outside of the housing 102. The holder 308 may be attached to the housing 102 in any number of ways including, for example, a weld. Alternatively, the holder 308 may be integrally formed as part of the housing 102

The housing 208 may also include an extension 306. One of the rollers 104 (e.g., the roller with the axis of rotation parallel to the surface supporting the hose storage system 100) may be rotatably mounted to the extension 306. The roller 104 may be rotatably mounted to the extension 306 in any number of ways including, for example, with a nut/bolt combination.

In one embodiment, a nut and a washer may be disposed on the shaft 210, and the nut is tightened against the washer and the pulley 212*d*. The tightened nut may further press the plurality of pulleys 212 and the spacers 222 together. Additional nuts and/or washers may be provided along the shaft 210 (e.g., at each pulley/spacer interface). In one embodiment, the first pulley assembly 200 includes stoppers (e.g., rubber stoppers) positioned on the bottom of the housing 208. The stoppers may prevent a metal-to-metal collision between the first pulley assembly 200 and the second pulley assembly 202 when the second pulley assembly moves towards the first pulley assembly 200 during operation of the hose storage system 100, as described below.

The top view of FIG. 3 shows an exemplary shape of a cross-section of the housing 102. The housing 102 of FIG. 3 is heart shaped. The cross-section of the housing 102 may be other shapes including, for example, square, rectangular, circular, or another shape.

FIG. 4 shows a perspective view of one embodiment of the first pulley assembly 200 and the second pulley assembly 202 for the hose storage 100 system of FIG. 2. The second pulley assembly 202 includes a housing 400, a shaft 402, a plurality of pulleys 404 (e.g., pulleys 404*a*, 404*b*, and 404*c*), and a brake assembly 406. In the embodiment shown in FIG. 4, the housing 400 of the second pulley assembly 202 is slidably attached to the rail 204 (see FIG. 5) beneath the first pulley assembly 200. In one embodiment, the housing 400 of the second pulley assembly 202 is suspended from the first pulley assembly 200 (e.g., via the hose 118 wrapped around the plurality of pulleys 212 and the plurality of pulleys 404).

The housing 400 includes a top 408, a bottom 410, a first side 412, a second side 414, a front 416, and a back 418. The housing 400 of the second pulley assembly 202 of the embodiment shown in FIG. 4 is rectangular in shape. For example, the housing 400 is a rectangular tube or a square tube. In one embodiment, the housing 400 is formed from sheet metal like the housing 208 of the first pulley assembly 200. The rectangular tube housing 400 may be oriented such that the top 408 and the bottom 410 are open. One or more other sides may be completely open (e.g., the front 416). In one embodiment, none of the sides are completely open, and one or more sides are removable (e.g., the bottom 410). Other sides (e.g., the second side 414) may include one or more openings 420 machined out of the housing 400, for example, for operation of the brake assembly 406. The housing 400 may be any number of other shapes and/or may be formed by individual sides or plates attached together via one or more types of fasteners (e.g., nut/bolt combinations and/or screws).

The housing 400 may be made of any number of materials. For example, the housing 400 may be an aluminum rectangular tube. Alternatively or additionally, the housing 400 may be made of one or more other materials. For example, all or less than all of the sides of the housing 400 may be made of plastic (e.g., UHMW polyethylene). Other materials may be used.

The shaft 402 extends across the entire width of the housing 400, through openings in the first side 412 and the second side 414. The shaft 402 is cylindrical in shape and may be made of any number of materials including, for example, steel or UHMW polyethylene. The shaft 402 may be any number of dimensions. For example, the shaft 402 may be 7.0 mm in diameter and may extend across the entire housing 400. Other configurations may be provided.

The shaft 402 may be attached to the housing 400 such that the shaft 402 does not translate or minimally translates along a direction in which the shaft 402 extends from the first side 412 to the second side 414 and/or such that the shaft 402 does not rotate relative to the housing 400, for example. The shaft 402 may be a bolt that is threaded on one side, and a nut may be used at the threaded side, such that the shaft 402 does not translate and/or rotate relative to the housing 400 of the second pulley assembly 202. In one embodiment, the openings in the first side 412 and the second side 414 may include bearings in which the shaft 402 rotates. In another embodiment, the shaft 402 is threaded on both ends, and nuts (e.g., cap nuts) are used to attach the shaft 402 to the housing 400.

In the embodiment shown in FIG. 4, the plurality of pulleys 404 includes three pulleys 404 (e.g., pulleys 404*a*, 404*b*, and 404*c*) positioned along the shaft 402. The plurality of pulleys 404 may include one fewer pulley than the plurality of pulleys 212 of the first pulley assembly 200. In other embodiments, the plurality of pulleys 404 includes more or fewer pulleys (e.g., only one pulley 404) positioned on the shaft 402. The plurality of pulleys 404 may be spaced along the shaft 402 using, for example, spacers 422 (e.g., two spacers 422, each between a respective pair of pulleys of the plurality of pulleys 404). Other spacers may be provided outside the outermost pulleys of the plurality of pulleys 404. The spacers 422 may be made of any number of materials, may be any number of shapes, and may have any number of dimensions. For example, at least some of the spacers 422 are cylindrical and have an inner diameter of 7.0 mm and an outer diameter of 1.0 inch. The spacers 422 may have variable width. For example, the spacer 422 closest to the second side 414 may have a greater width than the other spacer(s) 422. The spacers 422 may provide pressure on or mechanical interlocking among the plurality of pulleys 404 such that the plurality of pulleys 404 do not translate along the shaft 402. Each pulley of the plurality of pulleys 404 may rotate relative to the other pulleys of the plurality of pulleys 404.

Each pulley of the plurality of pulleys 404 may be made of any number of materials including, for example, aluminum or plastic (e.g., UHMW polyethylene). Other materials may be used for the plurality of pulleys 404. Each pulley of the plurality of pulleys 404 may have any number of dimensions. For example, for each pulley of the plurality of pulleys 404, a groove 424 between two annular flanges 426 of the pulley 404 may be sized to fit a particularly dimensioned hose to be stored in the hose storage system 100 (e.g., the hose 118). The flanges 424 may be dimensioned such that the particularly dimensioned hose remains on the plurality of pulleys 404 during operation of the hose storage system 100. In one embodiment, the groove 424 and the flanges 426 may be sized such that a number of different sized hoses may be stored in the hose storage system 100.

In one embodiment, a nut and a washer may be disposed on the shaft 402, and the nut may be tightened against the washer and the pulley 404*c*. The tightened nut may press the plurality of pulleys 404 and the spacers 422 together (e.g., against the first side 412). Additional nuts and/or washers may be provided along the shaft 402 (e.g., at each pulley/spacer interface). In one embodiment, the second pulley assembly 202 includes stoppers (e.g., rubber stoppers) positioned on the top 408 of the housing 400. The stoppers may prevent a metal-to-metal collision between the second pulley assembly 202 and the first pulley assembly 200 when the second pulley assembly moves towards the first pulley assembly 200 during operation of the hose storage system 100.

The brake assembly 406 includes a shaft 428. The shaft 428 may, for example, extend through the opening 420 and out of the second side 414 of the housing 400 and may be used by a user to engage and disengage the brake assembly 406. The brake assembly 406 may operate on one or more pulleys of the plurality of pulleys 404 (e.g., the pulley 404*c*). In other embodiments, the brake assembly 406 may be positioned on a different side of the second pulley assembly 202 (e.g., the shaft 428 may extend out of the first side 412 of the housing 400). In yet another embodiment, the brake assembly 406 does not include a shaft, and the second side 414 does not include the one or more openings for the shaft.

FIG. 5 shows a perspective view of the second pulley assembly 202 of FIG. 4. FIG. 5 shows the slidable attachment of the second pulley assembly 202 to the rail 204 and the brake assembly 406. The second pulley assembly 202 includes a slider 500 attached to the housing 400. The slider 500 may, for example, be attached to the back 418 of the housing 400 using, for example, screws or nut/bolt combinations. Alternatively, the slider 500 may be welded or adhered to the back 418 of the housing 400. The slider 500 may be attached to the housing 400 in any number of other ways, or the slider 500 may be integrally formed as part of the housing 400. The slider 500 may be made of any number of materials. For example, the slider 500 may be made of plastic (e.g., UHMW plastic).

In one embodiment, the slider 500 is formed by two extensions 502 that extend away from the back 418 of the housing 400. The extensions 502 include slots 504, such that the flanges of the rail 204 are positioned in the slots 504, and the second pulley assembly 202 is movable along the rail 204 in a direction towards the first pulley assembly 200 and in a direction away from the first pulley assembly 200.

In another embodiment, the slider 500 is square or rectangular tubing with plastic inserts to prevent metal-to-metal contact. Such a slider 500 may include a slot such that the slider 500 is positionable around at least a portion of the rail 204 (e.g., a portion of the cross-section of the rail 204 or all of the cross-section of the rail 204). This positioning allows the slider 500 to slide along the rail 204, such that the second pulley assembly 202 is movable relative to the rail 204 in a direction towards the first pulley assembly 200 and in a direction away from the first pulley assembly 200.

The brake assembly 406 slows and/or prevents movement of the second pulley assembly 202 relative to the rail 204. The brake assembly 406 includes the shaft 428 and a brake 506. The shaft 428 extends through and is movable within the opening 420 in, for example, the second side 414 of the housing 400. In one embodiment, the shaft 428 is an aluminum shaft or rod. The shaft 428 may be made of other materials (e.g., a single piece of UHMW plastic). In another embodiment, the shaft 428 may include a bolt, a cylindrical cover (e.g., a UHMW plastic cylindrical cover) around a portion of the bolt, one or more nuts tightened on one or more sides of the cylindrical cover, respectively, and one or more washers positioned along the bolt. Other shafts may be provided. For example, the shaft 428 may be made entirely of a single material (e.g., a single piece of UHMW plastic). In one embodiment, the brake assembly 406 does not include a shaft.

The shaft 428 is connected to the brake 506. In the embodiment shown in FIG. 5, the brake 506 is in the form of an extension (e.g., a tab or plate), but other brakes may be used. The brake 506 may be made of any number of materials including, for example, plastic (e.g., UHMW plastic) and/or metal (e.g., steel). In one embodiment, the shaft 428 is connected to the brake 506 via a weight 508 (e.g., made of a metal such as steel) that biases the brake 506 in a braking position. The bolt of the shaft 428, for example, may screw into a threaded opening of the weight 508 to connect the shaft 428 to the weight 508. A screw extends through another opening 510 in the weight 508 and extends at least partially through the brake 506 to connect the weight 508 to the brake 506. Other connectors (e.g., an adhesive)

may be used to connect the shaft 428 to the weight 508, and to connect the weight 508 to the brake 506.

The shaft 428 may be moved (e.g., slid) from a first position within the opening 506, which corresponds to an unlocked position of the brake 506, into a second position within the opening 506, which corresponds to a locked position of the brake 506 (shown in FIG. 5), to slow down and/or stop movement of the second pulley assembly 202 relative to the rail 204. In the embodiment shown in FIG. 5, the pulley 404c includes a slot into which the brake 506 is positionable. Other pulleys 404 may include one or more slots. When the brake 506 is positioned within the slot of the pulley 404, a position of the second pulley assembly 202 may be fixed relative to the rail 204. The weight 508 keeps pressure on the brake 506 such that the brake 506 remains within the slot of the pulley 404c. When the second pulley assembly 202 is moving relative to the rail 204 at a particular speed, the brake 506 may not engage with the slot within the pulley. The particular speed at which the slot is engageable may be set based on the size and/or shape of the slot, and/or the size and/or shape of the brake 506. In one embodiment, the grooves 424 of the plurality of pulleys 404, respectively, include a layer of material that helps retain the brake 506 within the slot in the pulley 404c. The layer of material may be, for example, a layer of rubber or a non-skid spray (e.g., a rubber band). Other materials may be used for the layer of material.

The brake assembly 406 may also include a magnet 512. The magnet 512 may be attached to the housing 400 of the second pulley assembly 202 via a magnet housing 514, for example. The magnet housing 514 supports the magnet 512 and is connected to the housing 400 in any number of ways including, for example, via welding and/or with one or more connectors. In one embodiment, the magnet 512 is attached directly to the housing 400 of the second pulley assembly 202.

In one embodiment, a side 516 of the brake 506 (e.g., a side facing the pulley 404c) includes a plate that may be moved into contact with the magnet 512. The plate is attached to the brake 506, for example, with a nut/bolt combination. The plate may be attached to the brake 506 in any number of other ways including, for example, with an adhesive. The plate may be made of any number of magnetic metals including, for example, iron. The plate may be sized and shaped to match the size and shape of at least a portion of the brake 506 and/or the size and shape of the magnet 512, respectively. In one embodiment, the brake assembly 406 does not include the plate, and the brake 506 is made of a magnetic metal.

As shown in FIG. 5, the brake 506 is inserted into the slot in the pulley 404c, and the second pulley assembly 202 is unable to move relative to the rail 204. The opening 420 in the second side 414 of the housing 400 may have an irregular shape designed to facilitate movement of the shaft 428, and thus the brake 506, from the locked position into an unlocked position, and vice versa. When the shaft 428 and the brake 506 are moved from the locked position into the unlocked position, the magnet 512 engages with the plate, and the second pulley assembly 202 is able to move relative to the rail 204.

The position of the opening 116 (see FIG. 1) relative to the surface that supports the hose storage system 100 (e.g., the floor) helps keep hose stored in the hose storage system 100 (e.g., the hose 118) off of the floor, which makes use of, for example, an oxygen concentrator safer for both the user and caretakers. When the user needs to move around a room in which the hose storage system is positioned, the user or a movable patient device moving the patient (e.g., a transportation device) may apply a force to a portion of hose located outside of the hose storage system 100 (e.g., a portion of the hose 118) to release the hose 118, for example, from the hose storage system 100.

FIG. 6 shows one embodiment of a movable patient device that may apply the force to the hose 118 to remove hose 118 from the hose storage system 100. In the embodiment shown in FIG. 6, the movable patient device is a scooter 600 on which the user may ride. Other movable patient devices such as, for example, a wheel chair may be provided. Alternatively, the patient device may be stationary (e.g., a chair or a bed).

The scooter 600 includes a pipe 602 and a flexible hose 604. The pipe 602 is attached to a frame of the scooter 600 and extends in a direction away from a surface supporting the scooter 600 (e.g., the floor). The pipe 602 may be any number of dimensions and may be made of any number of materials. The pipe 602 may be sized to accept a number of different sized tubes within the pipe 602. For example, the pipe 602 is a 0.75 inch aluminum pipe. The height of the pipe 602 in combination with the operation of the hose storage system 100 and the location of the opening 116 keeps the hose 118, for example, off the ground.

The flexible hose 604 is attached to the pipe 602 at a top end 606 of the pipe 602. The flexible hose 604 may be attached to the pipe 602 in any number of ways including, for example, with a clamp, an adhesive, a friction fit, or another connector. The hose 118, for example, extends through the flexible hose 604, through the pipe 602, and out an opening (not shown) within the pipe 602, and connects to a nasal cannula. Alternatively, the hose 118 connects to the nasal cannula at or inside the pipe 602. The flexible hose 604 may prevent kinking of the hose 118, for example. The user wears the nasal cannula, which provides supplemental oxygen or airflow to the user. In one embodiment, the nasal cannula is connected to the hose 118, for example, via an interface or a flow meter.

As the user moves away (e.g., drives away using the scooter 600 or walks away) from the hose storage system 100, the force on the hose 118 causes a portion of the hose 118 stored in the hose storage system 100 to exit the opening 116 in the housing 102, aided by the one or more rollers 104.

As shown in FIG. 4, the hose 118, from the opening 116 in the housing 102 (FIG. 4 does not show the hose from the opening 116 to pulley 212d for clarity), wraps partially around pulley 212d and extends down to pulley 404c. The hose 118 wraps partially around pulley 404c and extends up to pulley 212c. The hose 118 wraps partially around pulley 212c and extends down to pulley 404b. The hose 118 wraps partially around pulley 404b and extends up to pulley 212b. The hose 118 wraps partially around pulley 212b and extends down to pulley 404a. The hose 118 wraps partially around the pulley 404a and extends up to pulley 212a. The hose 118 wraps partially around the pulley 212a and extends through the holder 308 or connects to the hose connector.

After passing through the holder 308, for example, the hose 118 extends out of the housing 102 to an oxygen concentrator, for example. In one embodiment, a portion of the housing 102 is indented inward to form a surface inside the housing 102 that is parallel to the floor. The surface includes an opening, through which the hose 118 extends. A rubber grommet, for example, may be provided at the opening through the surface to protect the hose 118 extending through the opening through the surface. The hose 118 then extends to the oxygen concentrator, for example, outside of the housing 102. In other embodiments, the hose storage system 100 is located in a housing of the oxygen concentrator or the oxygen concentrator is located within the housing 102 of the hose storage system 100.

As more and more of the hose 118 exits the hose storage system 100, the plurality of pulleys 212 and the plurality of pulleys 404 rotate, and the second pulley assembly 202 moves towards the first pulley assembly 200 along the rail 204. The amount of the hose 118 stored in the hose storage system 100 would thus decrease as the second pulley assembly 202 moves towards the first pulley assembly 200.

When the force applied to the hose 118, for example, is removed or lessened, the force of gravity on the second pulley assembly 202 causes the second pulley assembly 202 to move away from the first pulley assembly 200 along the rail 204, which causes at least a portion of the hose 118 to be pulled into the hose storage system 100, and the plurality of pulleys 212 and 404 to rotate. The brake 506 may be engaged to prevent the second pulley assembly 202 from moving away from the first pulley assembly 200 along the rail 204 due to the gravitational force on the second pulley assembly 202. If the second pulley assembly 202 is moving above a particular speed (e.g., defined by the size of the slot in the pulley 404c), the brake 506 may not engage.

The hose storage system 100 may be used to store other lengths of material (e.g., other cylindrically shaped lengths of tubing). For example, the hose storage system 100 may be used to store power cabling (e.g., an extension cord), a garden hose, or other cabling or hose.

FIG. 7 shows a flowchart of one embodiment of a method for providing a portion of a hose stored in a hose storage system to a user. The method may be performed using the hose storage system 100 shown in FIGS. 1-5 or another storage system. The method is implemented in the order shown, but other orders may be used. Additional, different, or fewer acts may be provided. Similar methods may be used for providing a portion of a hose stored in a hose storage system to a user.

The hose storage system includes a structure, and a lower pulley assembly and an upper pulley assembly supported by the structure. The lower pulley assembly includes one or more pulleys. The upper pulley assembly includes two or more pulleys. At least part of the upper pulley assembly is positionally fixed relative to the structure. The hose is wrapped partially around the two or more pulleys of the upper pulley assembly and partially around the one or more pulleys of the lower pulley assembly, and exits the hose storage system through an opening in the hose storage system.

In act 700, the lower pulley assembly is moved towards the upper pulley assembly in response to a force applied to the hose. The force applied to the hose may, for example, be the user pulling on the hose. Alternatively, an end of the hose may be attached to part of a movable patient device such as a wheel chair or a scooter, and the force applied to the hose may, for example, be the result of movement of the movable patient device. The movement of the lower pulley assembly towards the upper pulley assembly releases the portion of the hose through the opening in the hose storage system.

In act 702, the lower pulley assembly is moved away from the upper pulley assembly when the force applied to the hose is removed or lessened. The moving of the lower pulley assembly away from the upper pulley assembly is in response to gravity.

In act 704, the movement of the lower pulley assembly away from the upper pulley assembly is braked. The braking includes inserting a portion of a braking device of the lower pulley assembly into a slot in a pulley of the one or more pulleys of the lower pulley assembly.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A storage system for storing a length of a tubular structure, the storage system comprising:
   a support structure;
   a first pulley assembly comprising a plurality of first pulleys, at least a part of the first pulley assembly being translationally fixed relative to the support structure, the plurality of first pulleys being rotatable about a first axis of rotation; and
   a second pulley assembly translationally movable relative to the first pulley assembly and relative to the support structure, the second pulley assembly comprising at least one second pulley, the at least one second pulley being rotatable about a second axis of rotation,
   wherein the at least one second pulley comprises a plurality of second pulleys, the number of second pulleys being one less than the number of first pulleys,
   wherein the first pulley assembly comprises a first housing and a first shaft extending through the first housing, the plurality of first pulleys being rotatable about the first shaft defining the first axis of rotation,
   wherein the second pulley assembly comprises a second housing and a second shaft extending through the second housing, the at least one second pulley being rotatable about the second shaft defining the second axis of rotation,
   wherein the second pulley assembly includes a braking system, the braking system comprising:
   a shaft that is movable between a first position and a second position; and
   a tab connected to the shaft,
   wherein a pulley of the at least one second pulley comprises a slot into which a portion of the tab is insertable when the shaft is in the second position, and
   wherein the second pulley assembly is movable along the support structure when the shaft is in the first position, and the second pulley assembly is not movable along the support structure when the shaft is in the second position.

2. The storage system of claim 1, wherein the support structure comprises a rail along which the second pulley assembly is slidable.

3. The storage system of claim 2, wherein the first pulley assembly and the second pulley assembly both abut the rail, and
   wherein the second pulley assembly is slidable along the rail beneath the first pulley assembly.

4. The storage system of claim 2, wherein the support structure further comprises a housing, the first pulley assembly, the second pulley assembly, and the rail being disposed within the housing.

5. The storage system of claim 4, wherein the housing is stationary.

6. The storage system of claim 4, wherein the housing comprises an opening near, at, or adjacent a top edge of the housing, and wherein the hose storage system further comprises a roller attached to the housing, adjacent to the opening in the housing, the roller being rotatable about a third axis.

7. The storage system of claim 6, wherein the first pulley assembly further comprises a hose connector,
wherein the tubular structure is a hose, the hose at least extending from the hose connector, partially around a first pulley of the plurality of first pulleys, to a first pulley of the at least one second pulley, partially around the first pulley of the at least second pulley, to a second pulley of the plurality of first pulleys, and partially around the second pulley of the plurality of first pulleys, and
wherein the hose exits the housing through the opening after extending partially around a last pulley of the plurality of first pulleys.

8. The storage system of claim 1, wherein the first axis of rotation and the second axis of rotation are coplanar in a plane perpendicular to a surface that supports the hose storage system.

9. The storage system of claim 1, wherein the tubular structure is oxygen tubing or an electrical lead.

10. A hose storage system comprising:
a housing comprising an opening near, at, or adjacent to a top edge of the housing;
a rail extending along at least a portion of the housing;
at least two first pulleys rotatable about a first axis, the at least two first pulleys being fixed translationally relative to the rail; and
at least one second pulley rotatable about a second axis, the at least one second pulley being movable translationally relative to the rail beneath the at least two first pulleys, in a direction along the rail, such that the at least one second pulley is movable away from and towards the at least two first pulleys,
wherein the at least one second pulley comprises a plurality of second pulleys, the number of second pulleys being one less than the number of first pulleys,
wherein a hose is extendable at least from a first pulley of the at least two first pulleys, partially around the first pulley of the at least two first pulleys, to a first pulley of the at least one second pulley, partially around the first pulley of the at least one second pulley, to a second pulley of the at least two first pulleys, and partially around the second pulley of the at least two first pulleys, the hose exiting the housing through the opening,
wherein the at least two first pulleys are part of a first pulley assembly, the first pulley assembly comprising a first housing and a first shaft extending through the first housing, the at least two first pulleys being rotatable about the first shaft defining the first axis,
wherein the at least one second pulley is part of a second pulley assembly, the second pulley assembly comprising a second housing and a second shaft extending through the second housing, the at least one second pulley being rotatable about the second shaft defining the second axis,
wherein the first pulley assembly, the second pulley assembly, or the first pulley assembly and the second pulley assembly include a braking system configured to brake movement of the second pulley assembly relative to the first pulley assembly, the braking system comprising:
a shaft that is movable between a first position and a second position; and
a tab connected to the shaft,
wherein a pulley of the at least one second pulley comprises a slot into which a portion of the tab is insertable when the shaft is in the second position, and
wherein the second pulley assembly is movable along the rail when the shaft is in the first position, and the second pulley assembly is not movable along the rail when the shaft is in the second position.

11. The hose storage system of claim 10, wherein the housing is movable.

12. The hose storage system of claim 10, wherein the braking system further comprises:
a guide in the second housing,
wherein the shaft extends through the guide,
wherein the portion of the tab is insertable into the slot when the shaft is in the second position within the guide, and
wherein the second pulley assembly is movable along the rail when the shaft is in the first position within the guide, and the second pulley assembly is not movable along the rail when the shaft is in the second position within the guide, and the portion of the tab is inserted into the slot.

13. The hose storage system of claim 10, further comprising a roller attached to the housing, adjacent to the opening in the housing, the roller being rotatable about a third axis.

14. A method for extending a portion of a hose stored in a hose storage system to a user, the hose storage system comprising a structure, and a lower pulley assembly and an upper pulley assembly supported by the structure, the lower pulley assembly comprising one or more lower pulleys, the upper pulley assembly comprising two or more upper pulleys, wherein the one or more lower pulleys comprise a plurality of lower pulleys, the number of lower pulleys being one less than the number of upper pulleys, wherein the upper pulley assembly comprises a first housing and a first shaft extending through the first housing, the two or more upper pulleys being rotatable about the first shaft defining a first axis of rotation, wherein the lower pulley assembly comprises a second housing and a second shaft extending through the second housing, the one or more lower pulleys being rotatable about the second shaft defining a second axis of rotation, wherein the lower pulley assembly includes a braking system, the braking system comprising a shaft that is movable between a first position and a second position, and a tab connected to the shaft, wherein a pulley of the one or more lower pulleys comprises a slot into which a portion of the tab is insertable when the shaft is in the second position, and wherein the lower pulley assembly is movable along the structure when the shaft is in the first position, and the lower pulley assembly is not movable along the structure when the shaft is in the second position, the hose being wrapped partially around the two or more upper pulleys of the upper pulley assembly and partially around the one or more lower pulleys of the lower pulley assembly and exiting the hose storage system through an opening in the hose storage system, the method comprising:
moving the lower pulley assembly towards the upper pulley assembly, at least a part of which is positionally fixed relative to the structure, in response to a force applied to the hose,
wherein the movement of the lower pulley assembly towards the upper pulley assembly releases the portion of the hose through the opening in the hose storage system.

15. The method of claim 14, further comprising moving the lower pulley assembly away from the upper pulley assembly when the force applied to the hose is removed or lessened, the moving of the lower pulley assembly away from the upper pulley assembly being in response to gravity.

16. The method of claim 15, further comprising braking the movement of the lower pulley assembly away from the upper pulley assembly.

* * * * *